United States Patent [19]

Beuneche et al.

[11] Patent Number: 4,681,730
[45] Date of Patent: Jul. 21, 1987

[54] PROCESS AND DEVICE FOR DETECTING LEAKING NUCLEAR FUEL ELEMENTS IN A NUCLEAR ASSEMBLY

[75] Inventors: Daniel Beuneche, Collonges au Mont d'Or; Christian Mauvieux, Lyons; Pierre Amiet, Condrieu, all of France

[73] Assignee: Fragema, Courbevoie, France

[21] Appl. No.: 802,276

[22] Filed: Nov. 27, 1985

[30] Foreign Application Priority Data

Nov. 29, 1984 [FR] France ............... 84 18223

[51] Int. Cl.⁴ .................................. G21C 17/00
[52] U.S. Cl. ............................................ 376/252
[58] Field of Search .................................. 376/252

[56] References Cited

U.S. PATENT DOCUMENTS

| 3,936,348 | 2/1976 | Watcher et al. | 376/252 |
| 3,945,245 | 3/1976 | Stehle et al. | 376/252 |
| 4,016,749 | 4/1977 | Watcher | 376/252 |
| 4,126,514 | 11/1978 | Wonn | 376/252 |
| 4,149,932 | 4/1979 | Jacobs et al. | 376/249 |
| 4,193,843 | 3/1980 | Womack et al. | 376/252 |
| 4,443,402 | 4/1984 | Marini | 376/252 |
| 4,517,152 | 2/1985 | Pieper et al. | 376/252 |
| 4,554,128 | 11/1985 | Parker et al. | 376/252 |

FOREIGN PATENT DOCUMENTS

| 0081747 | 6/1983 | European Pat. Off. | 376/252 |
| 2538155 | 6/1984 | France | 376/252 |

Primary Examiner—Salvatore Cangialosi
Attorney, Agent, or Firm—Pollock, Vande Sande & Priddy

[57] ABSTRACT

An ultrasonic transducer carried by rod means of dimensions such that it may be inserted in the assembly between an end piece and the caps of the element, and a crossed movement moving mechanism for bringing the transducer above the different elements. It further comprises a mechanism for moving rod elements in the longitudinal direction of the fuel elements. The transducer is set up on rod elements with at least one degree of freedom about a shaft transversal to the fuel elements so as to be able to be applied flat against the end face of a cap.

7 Claims, 4 Drawing Figures

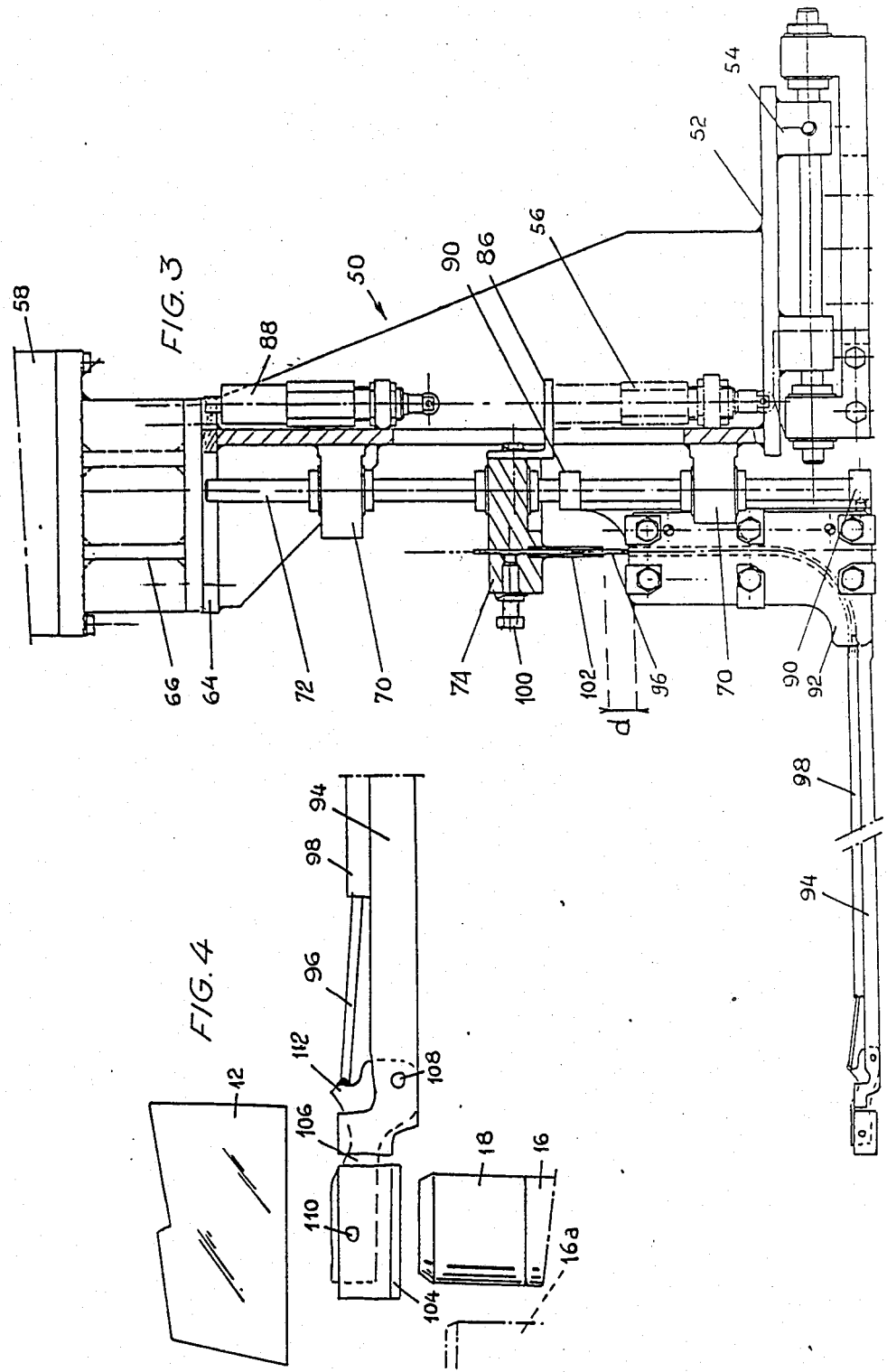

PROCESS AND DEVICE FOR DETECTING LEAKING NUCLEAR FUEL ELEMENTS IN A NUCLEAR ASSEMBLY

FIELD OF THE INVENTION

The invention concerns the detection of leaking fuel elements in a nuclear reactor fuel assembly of the type comprising a bundle of fuel elements or "rods", held in a rigid structure including end pieces connected together by braces and grids spaced apart along the braces. Each element is formed by a metal tubular sheath closed by gas tight caps, containing a stack of nuclear fuel pellets surrounded by a dry atmosphere of gas under pressure, when the sheath is fluid tight. The pellets are held in contact by a spring compressed between the stack and an end cap and placed in a plenum occupied by the gas under pressure.

BACKGROUND OF THE INVENTION

It is necessary to check the fuel assemblies extracted from the core of the reactor. The conventionally used method consists in measuring the activity released by an assembly when it is plunged in a fluid. But with this method it is only possible to check that the whole assembly is tight. It does not allow to detect which element or elements of a defective assembly is or are leaking.

Numerous methods for non-destructive testing of the fuel elements by using ultrasounds already exist. Among others, there is one (EP-A 0 115 231) which consists in the emission of a train of ultrasonic waves, fed into the sheath from one of its end parts, at a frequency selected so that they travel in the form of Lamb waves; the echoes are then detected and analyzed. Such detection is performed at frequencies whose range corresponds for one fraction to notable absorption by the water possibly contained in the sheath, and for another fraction to a reflection from the end of the spring, especially in case of pressurization.

This solution is perfectly satisfactory when the waves are emitted and received by the transducer placed on the end face of the cap which closes the fuel element. But up to now it has only been possible to control all the elements using such a process when one of the end pieces of the assembly has been previously removed, because of the presence of the braces, of a diameter substantially greater than that of the fuel elements, and the differences of level of the caps in the assembly which have sejourned in the reactor. Unfortunately, the replacement of an end piece, in many assemblies, represents a delicate operation.

To overcome the need of dismantling, devices have also been proposed (FR-A-2 341 183) allowing a transducer to be introduced into the bundle, transversely to the axis thereof, and to be applied against the side wall of the sheath of any one of the fuel elements. By advancing the transducer all the elements of the same network may be checked. The checking time may be further reduced by providing several transducers, carried by a comb shaped piece. But the use of transducers applied against the side wall of the sheath gives less favorable results than that of sensors applied against a cap and leaves unsolved the problem of the masking of some elements by braces; in addition, this use is independent of the position of the water in the element.

SUMMARY OF THE INVENTION

It is an object of the invention to provide a process and a device for detecting leaking elements in an irradiated assembly giving better answers than those known especially in transducer placed at the end of each element and having good contact therewith.

To this end, the invention proposes a process of the above defined type, characterized in that, in the gap between one of the end pieces of an irradiated assembly and the fuel elements, a transducer is introduced through rod means movable transversaly to the elements, until the transducer is above the cap of an element; the rod means are moved in the longitudinal direction of the assembly so as to apply the transducer against the end face of the cap of the element to be checked before emitting a train of ultrasonic waves and detecting the echoes; the transducer is raised towards the end piece through rod means; the rod means are then removed for repeating the operations so as to check new elements.

The rod means are advantageously introduced in a diagonal direction of the elements network, when this network is square, which is the most general case; it is in fact in this orientation that the presence of the braces is the least obstructive. To have access to all the elements, despite the presence of the braces, the test may be carried out in two or four steps, the assembly being rotated by 90° about its longitudinal axis after each step.

The invention also provides a device for implementing the above defined process. This device for ultrasonic detection of the leaking fuel elements in a nuclear reactor fuel assembly comprising a bundle of fuel elements held in a rigid structure including end pieces connected together by braces, comprising an ultrasonic transducer carried by rod means of dimensions such that it may be inserted in the assembly between an end piece and the caps of the elements, and comprising crossed movement maneuvering means for bringing the transducer above the different elements, is characterized in that it includes means for moving the rod means in the longitudinal direction of the elements, and in that the transducer is mounted on the rod means with at least one degree of freedom about an axis transversal to the elements so as to be applied flat against the end face of a cap.

BRIEF DESCRIPTION OF THE DRAWINGS

The invention will be better understood from reading the following description of a particular embodiment, given by way of non limitative example. The description refers to the accompanying drawings in which:

FIGS. 2 and 3 show a part belonging to the device allowing to movement of the detector in direction Z, respectively in section through planes II—II of FIG. 1 and III—III of FIG. 2;

FIG. 4 is an enlarged front view showing one possible method of articulating the transducer to the part allowing the movement in direction Z.

DETAILED DESCRIPTION

Figure 1:
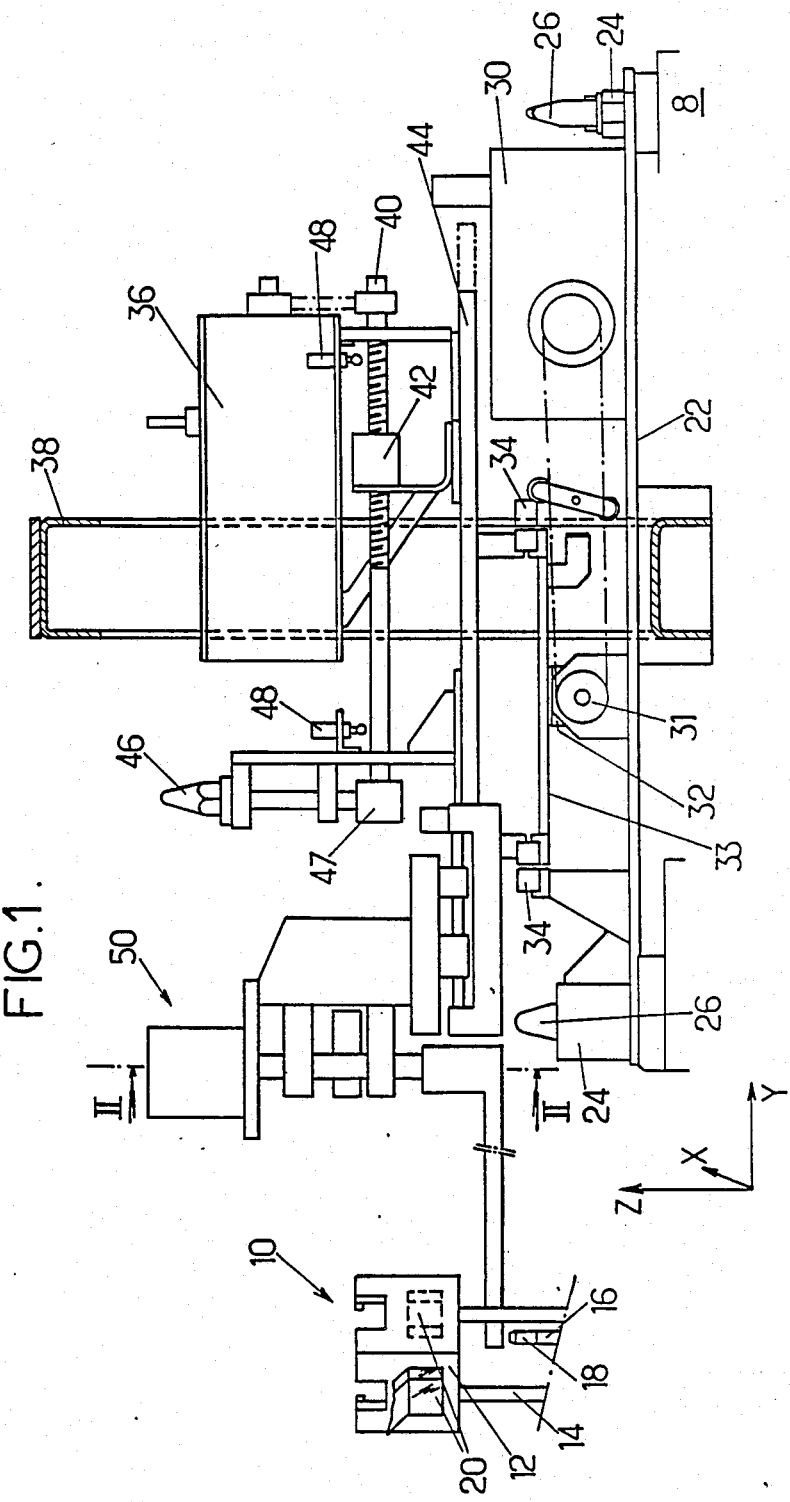
FIG. 1 is a general diagram of a device according to the invention, the directions of movement X, Y and Z being shown.

The device shown schematically in FIG. 1 is intended to be placed on a structure 8 provided in a pool in the vicinity of an assembly 10 to be checked. FIG. 1 shows the silhouette of the top part of such an assembly 10, comprising an end piece 12 on which braces 14 are fixed. A single element 16, closed by a cap 18, has been shown. The plate 8 compises jaws 20 for clamping the end piece 12 and a mechanism for rotating the assembly in the open jaws, around its vertical axis.

Another method may consist of a simple suspension from a lifting equipment having a turning hook associated with the same jaws 20.

The detection device, properly speaking, comprises a framework 22 made from several welded parts, having sleeves for centering on studs 26 of the support 8 and a handling gantry 38.

The parts of the device for moving the transducer respectively in the directions X, Y and Z will now be described.

The first two parts may be of any conventional construction used for providing crossed movements. In the embodiment illustrated, the X movement part comprises a motor 30 whose output shaft drives a screw 31 threadedly connected by recirculating balls to a ring 32 fastened to a support plate 33. This plate is provided with shoes sliding on guide slides 34 in the direction X, which, as will be seen, is transversal to the direction for introducing the transducer into the assembly. The part for movement in direction Y, comprises a motor 36, of the step by step type, like motor 30, and whose output shaft drives a screw 40. A ball socket 42 mounted on screw 40 drives a table 44 which slides over slides (not shown). For manually removing the transducer in case of an operating defect in motor 36, a manual control is provided. It comprises a control square 46 driving screw 40 through a bevel gear 47. Limit switches 48 will generally be provided for actuation by socket 42 when this latter arrives at the end of its working course. The X movement assembly also generally comprises limit switches. Finally, the motors of the two parts are associated with movement measurement coders (not shown).

Figure 2:
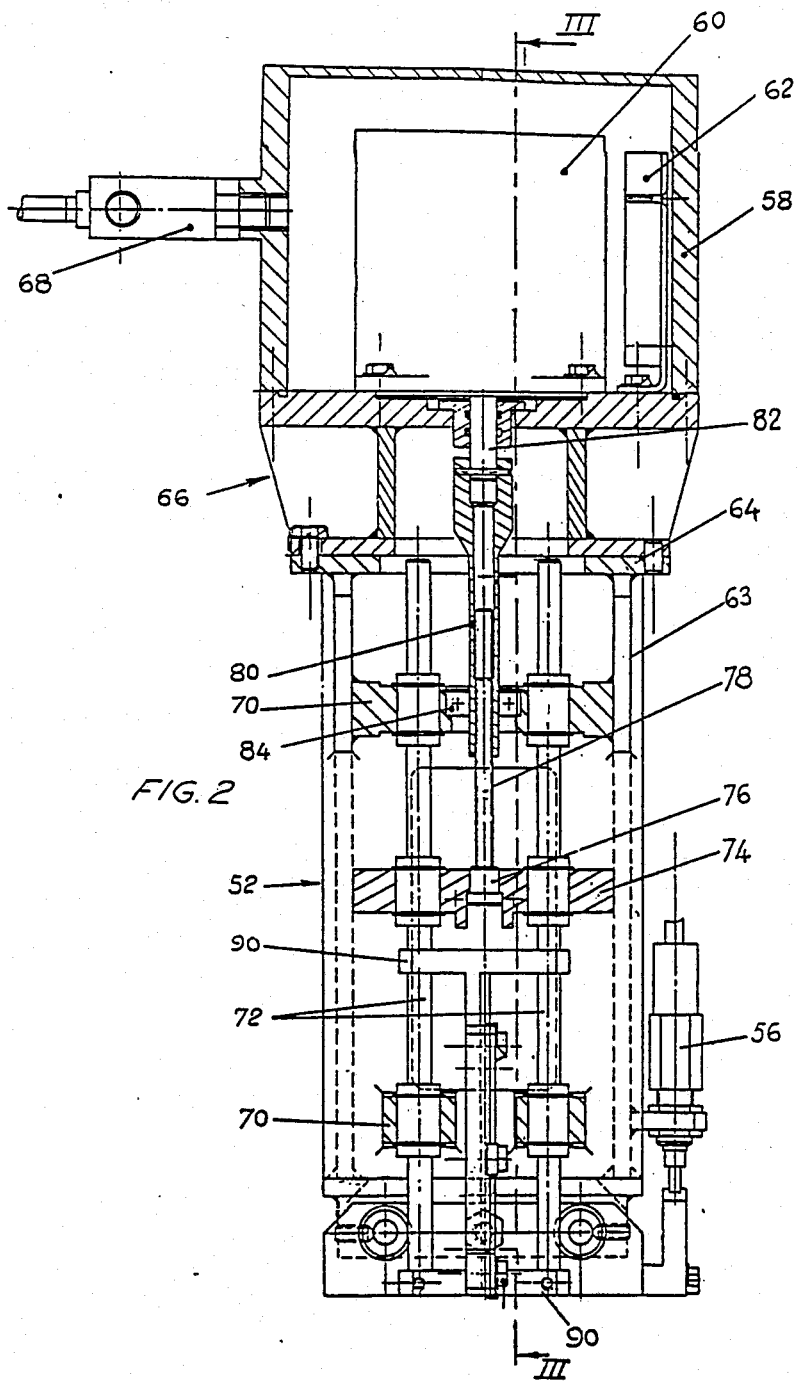

The part 50 for moving in direction Z, (i.e., along the axis of assembly 10) is shown only by its contour in FIG. 1. As shown in FIGS. 2 and 3, this part comprises a frame 52 supported by table 44 through a resilient device 54 capable of sliding in the direction in which the transducer is introduced into the assembly and absorbing the shocks caused by engagement of the transducer, so as to avoid damage to the equipment or the elements to be checked. A limit switch 56 detects the sliding and stops motor 36 in case of an engagement causing sliding.

Frame 52 of part 50 is formed by a welded structure comprising a slide carried by table 44, brackets 53 and a flange 64. On flange 64 is fixed, for example by means of screws, a second structure 66 made from crossed plates welded together, forming the bottom of a sealed case 58 which contains a step by step drive motor 60 and electric connections 62 for supplying control pulses to motor 60. The pressurization fluid arrives in this case through a fluid tight connection 68 (FIG. 2).

Frame 52 (FIG. 3) comprises transverse plates 70 for guiding a mobile equipment in direction Z. This equipment comprises two columns 72 connected together by a connecting piece 74 and sliding in ball bearings carried by plates 70. Plate 74 is supended from the end piece 76 of a threaded rod 78 secured against rotation and engaged in a tapped tube 80 keyed to the output shaft 82 of motor 60. A bearing 84 carried by the upper plate 70 provides guiding of the rotary tube 80.

The connection piece 74 has a finger 86 (FIG. 3) for tripping a contactor 88 carried by a frame 52 when the mobile assembly arrives at the top end of its travel.

A part, which, will be called hereafter "sword" because of its shape, will be called hereafter "sword", comprises a vertical plate 92 fixed to columns 72 by collars 90 and a metal rod 94 of rectangular section locked on plate 92 so as to be directed in direction Y. In the plate is formed a groove for guiding a cable 96, extended by a sheath 98 fixed to rod 94. The groove is covered by a plate preventing the cable from escaping. The end of cable 96 is fixed by a screw 100 to the connecting piece 74 and is held in position over only a fraction of its length by a guide 102. Thus, the cable 96 remains free over a length d.

The end part of rod 94 (FIG. 4) carries a transducer 104 through a double articulation allowing the transducer to move freely vertically with respect to the rod and guaranteeing clean engagement of the transducer against each cap of elements 18. The double articulation is provided by fork 106 mounted for rotation on a shaft 108 carried by the rod and on which the transducer rotates around a shaft 110 parallel to the first one. The cable 96 is fixed, for example by welding, to a projection 112 on the fork 106 offset with respect to shaft 108.

The operation of the device is as follows. The assembly to be checked is positioned in the mechanism, or suspended from its handling tool, allowing it to be rotated around its vertical axis between the jaws 20 for positioning piece 10 with respect to the detection device shown schematically in FIG. 1. With the device in position, and the "sword" withdrawn in direction Y, the dimensional characteristics of the assembly are stored in a control system of the device, then the checking sequence begins.

Motor 30 is actuated to bring the "sword" opposite to a diagonal network of elements to be checked. Motor 30 can be started and stopped automatically by a Program Logic Controller (PLC), whose input signal is provided by a coder associated with motor 30. With the position along Z of the "sword" such that transducer 104 and rod 94 may be reliably engaged in the free space between the end piece 12 and the elements, motor 36 is in its turn actuated to bring the transducer above a first element 16 to be checked. The parts are then arranged as shown in FIG. 4. Motor 60 is then actuated in its turn to lower the "sword". If this latter stops because the bottom of rod 94 abuts against an obstacle such as an element placed in front of the one to be checked, the connecting piece 74 continues to descend slightly. Cable 96 then slides in its sheath 98 and allows the transducer 104 to rock until it comes into contact with the cap 18 of the elements 16 to be checked. Once piece 74 is in its turn immobilized, the end piece 76 is freed therefrom and can continue to descend until the motor 60 stops, controlled by the PLC.

The ultrasonic exploration is then carried out using a method which may be the one described in document EP-A-0 115 231 already mentioned.

The "sword" is then raised, by motor 60, up to a level such that it may freely pass through the space between the elements and the end piece 12. The transducer is advanced one step in the direction Y and the sequence is repeated.

Because of the presence of the braces, access to all the elements cannot be obtained through a single diagonal direction of the assembly 10. Consequently, the "sword" will be removed once a fraction of the elements have been checked. The assembly will be rotated by at least once 90° and another fraction of the elements will be checked.

It can be seen that, because of the rocking mounting of the transducer 104, the active face of the transducer will always be applied flat against the end face of cap 18. Moreover, because the transducer may continue its downward movement if the rod should come into abutment, it is possible to test one element masked by another such as element 16a, in FIG. 4.

We claim:

1. A process for detecting leaking fuel elements in an irradiated fuel assembly comprising a bundle of fuel elements held in a rigid structure including end pieces connected together by braces, each of said fuel elements having a fluid-tight sheath, a stack of nuclear fuel pellets in said sheath and an end cap closing an end of said sheath defining a plenum chamber with said sheath and stack, comprising the steps of:
    (a) providing rod means carrying an ultrasound transducer on an end thereof,
    (b) introducing said transducer by moving said rod means transversely to said fuel elements into a gap between one of said end pieces and the fuel elements until the transducer is above the cap of an element,
    (c) moving said rod means in the longitudinal direction of said assembly so as to apply said transducer against an end face of the cap of the fuel elements to be checked,
    (d) emitting a train of ultrasonic waves into the end cap and detecting echoes thereof,
    (e) moving the transducer away from said end cap by said rod means and repeating steps (c) and (d) so as to check new elements.

2. a process according to claim 1, wherein said fuel elements are distributed in a square network and the said rod means are introduced in a diagonal direction of the said network.

3. A process according to claim 2, wherein said assembly is rotated by 90° about its longitudinal axis when a predetermined number of said fuel elements have been checked, to allow other ones of said fuel elements to be checked in their turn.

4. A device for detecting leaking fuel elements in an irradiated fuel assembly comprising a bundle of said fuel elements held in a rigid structure including end pieces connected together by braces, each of said fuel elements having a fluid tight sheath, stack of nuclear fuel pellets in said sheath and an end cap closing an end of said sheath and stack, said device comprising:
    (a) an ultrasonic transducer carried by rod means of dimensions such that they can be inserted into said assembly between one of said end pieces and caps of said elements,
    (b) crossed movement maneuvering means for bringing said transducer above said fuel elements, wherein said maneuvering means comprise means for moving the rod means in a direction transversal to the elements between said one of said end pieces and the caps of said elements and in the longitudinal direction of the elements and wherein the transducer is fixed on said rod means with at least one degree of freedom about a shaft transversal to the element so as to be able to be applied against the end face of caps of said elements.

5. A device according to claim 4, wherein said transducer is connected to said rod means by a fork rotating on the rod means around the shaft and having a pivoting connection with the transducer around a second shaft parallel to said first shaft.

6. A device according to claim 5, wherein the said fork is connected by a flexible connection to a piece movable by a motor for moving said rod means in a longitudinal direction, after said rod means come into abutment.

7. A device according to claim 4, wherein said crossed movement moving means comprise, at least for the direction of engagement of said rod means in said assembly, a manual emergency control mechanism.

* * * * *

UNITED STATES PATENT AND TRADEMARK OFFICE
CERTIFICATE OF CORRECTION

PATENT NO. : 4,681,730

DATED : July 21, 1987

INVENTOR(S) : Beuneche et al.

It is certified that error appears in the above-identified patent and that said Letters Patent is hereby corrected as shown below:

On the title page, item [73], the name of the assignee should be --Framatome et Cogema Dite Fragema--.

Signed and Sealed this

Thirtieth Day of April, 1991

*Attest:*

HARRY F. MANBECK, JR.

*Attesting Officer*  Commissioner of Patents and Trademarks